United States Patent [19]

Meyer

[11] 4,035,645
[45] July 12, 1977

[54] RADIATION MONITOR FOR AN IRRADIATION INSTALLATION

[75] Inventor: Rudolf Meyer, Erlangen, Germany

[73] Assignee: Siemens Aktiengesellschaft, Berlin & Munich, Germany

[21] Appl. No.: 651,281

[22] Filed: Jan. 22, 1976

[30] Foreign Application Priority Data

July 28, 1975 Germany .......................... 2533698

[51] Int. Cl.² .......................................... G01T 1/42
[52] U.S. Cl. ............................... 250/355; 250/336
[58] Field of Search ................... 250/336, 354, 355

[56] References Cited

U.S. PATENT DOCUMENTS

| | | | |
|---|---|---|---|
| 3,906,233 | 9/1975 | Vogel | 250/355 |
| 3,953,736 | 4/1976 | Kubisiak | 250/336 |
| 3,959,653 | 5/1976 | Lee | 250/336 |

Primary Examiner—Harold A. Dixon
Attorney, Agent, or Firm—Hill, Gross, Simpson, Van Santen, Steadman, Chiara & Simpson

[57] ABSTRACT

A radiation monitor for an irradiation or exposure installation for the presetting of a radiation dose which is to be applied and the limiting thereof to a preset reference value, including a dose rate frequency converter which is connected to a radiation detector exposed to the radiation of the irradiation installation; an impulse counter connected to the output of the dose rate frequency converter and having a thereto-connected presettable digital comparator, and an automatic switch-off device which is controllable through intermediary of the digital comparator upon reaching of the preset reference value.

3 Claims, 2 Drawing Figures

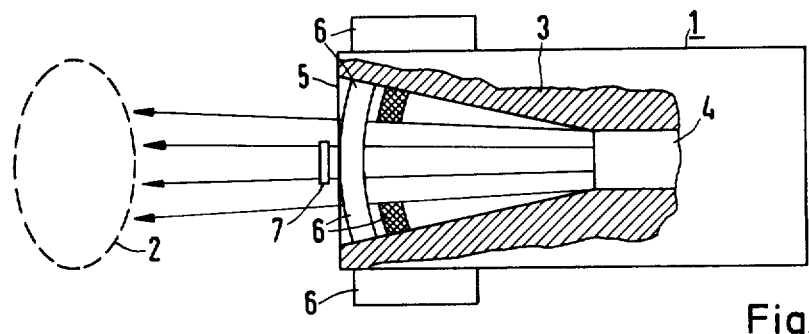
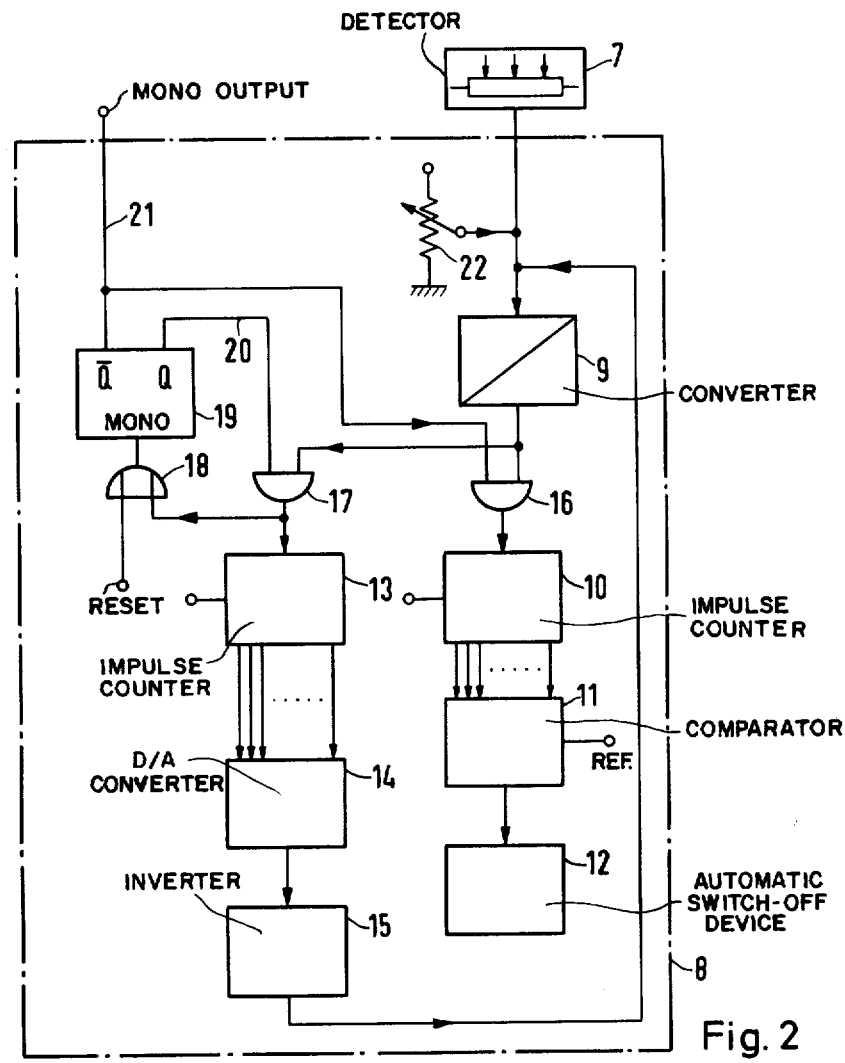

RADIATION MONITOR FOR AN IRRADIATION INSTALLATION

FIELD OF THE INVENTION

The present invention relates to a radiation monitor for an irradiation or exposure installation for the presetting of a radiation dose which is to be applied and the limiting thereof to a preset reference value, including a dose rate frequency converter which is connected to a radiation detector exposed to the radiation of the irradiation installation; an impulse counter connected to the output of the dose rate frequency converter and having a thereto-connected presettable digital comparator; and an automatic switch-off device which is controllable intermediary of the digital comparator upon reaching of the preset reference value.

DISCUSSION OF THE PRIOR ART

A radiation monitor of the above-mentioned type is utilized in an irradiation installation which is employed in the medical technology. The dose rate frequency converter produces an frequency in this installation which is proportional to the current flowing through the radiation detector. The impulse counter sums up the impulses so that its count position corresponds to the presently accumulated impulse number and thereby corresponds to the presently applied dose. At a count position which corresponds to that preset at the digital comparator in the preselection of the dosage reference value, the incident impulse is connected through by the digital comparator and is utilized for the control of the automatic switch-off or disconnect device. The exactness with which the irradiation installation switches-off after application of the preset radiation dosage, is subjected to long-term and short-term fluctuations. These fluctuations which are designated by the term "drift" are based on changes in the parameters of the emloyed electronic components. They may also be caused through environmental influences, in particular the temperature, or caused by aging.

SUMMARY OF THE INVENTION

Accordingly, it is an object of the present invention to increase the exactness which the radiation monitor will switch off irradiation or exposure installations upon the reaching of a preset dose reference value. Hereby, the operating requirements are to be maintained as low as possible. In a radiation monitor of the above-mentioned type, a second impulse counter having a digital analog converter connected to the output thereof is connected to the dose rate frequency converter for the drift correction of the electronic components, and in which the output of the digital analog converter is reconveyed through a polarity inverter to the input of the dose rate frequency converter. This circuit arrangement facilitates that the impulses which are received at the second impulse counter at switched-off radiation, based under these conditions practically on only a drift of the electronic components, can be reconverted into an analog electrical signal and to conduct this again, at a reversed polarity, to the analog input of the dose rate frequency converter within the context of effecting a compensation for the drift. Through the total summing up of the impulses in the second impulse counter this analog compensating signal increases for so long until the drift has been compensated and no further inpulses are longer received at the input of the second impulse counter. From then on there also no longer varies the amount of the analog signal which is transmitted to the input of the dose rate frequency-converter from the polarity inverter. The measurement which is carried out immediately subsequent to this balancing is thus effectuated without any drift errors.

It is namely known in electronic voltmeters, and also in other electronic measuring instruments, to short-circuit the measuring input, to measure the interference or static signal at the output of the measuring or test amplifier, to store analogously and to reconvey to the measuring input at a reversed polarity. However, this procedure has the disadvantage that the stored analog static signal varies significantly in its value within the passage of a few seconds. As a result, this type of drift compensation is suited only for short measuring periods within the range of seconds, but not for irradiation installation having measuring periods of up to 10 minutes. A further disadvantage of the known analog drift compensation lies in that it is not concerned with the drift of the dose rate frequency converter.

The drift correction may also be rendered automatic when, in an advantageous further feature of the invention, there is respectively connected an AND-gate ahead of the input of each of the two impulse counters, and a monostable flip-flop being connected in parallel with the input of the second impulse counter across an OR-gate, and in which the second input of the AND-gate connected ahead of the first impulse counter is connected to the output of the monostable flip-flop supporting a signal in the stable condition, and a second input of the AND-gate connected ahead of the second impulse counter is connected to the therewith inverted output of the monostable flip-flop. Through these additional components there is obtained that the first impulse counter remains switched off for so long upon the actuation of the radiation monitor through the AND-gate until the drift compensation has been carried out. As soon as this is the case, meaning when during the time constants of the monostable flip-flop no pulses are no longer received any further, which will prevent this from reaching its stable condition, this will set free the input of the first impulse counter through its AND-gate upon reaching its stable condition and concurrently will block the AND-gate for the second impulse counter through its inversed output in its stable condition. The found digital compensation values thus remain, and thereby also the corresponding analog signal received at the output of the digital analog converter.

BRIEF DESCRIPTION OF THE DRAWINGS

Reference may now be had to the following detailed description of an exemplary embodiment of the invention, taken in conjunction with the accompanying drawings; in which:

FIG. 1 illustrates a longitudinal sectional view through an irradiation installation shown in a considerably simplified and schematic representation; and FIG. 2 illustrates the schematic circuit block diagram representative of the construction of the radiation monitor.

DETAILED DESCRIPTION

Ascertainable in FIG. 1 of the drawings is an irradiation or exposure installation for ionizing radiation and an object 2 which is to be irradiated, which may also represent a patient. The irradiation installation contains a radiation source 4 which is encompassed by a protective radiation shielding 3 such as, for example, a source carrier for a radioisotope, an X-ray tube, or an accelerating tube of a linear accelerator, or a betatron. The outlet or delivery aperture 5 for the radiation is closeable by means of a shutter-control system 6 (Bucky diaphragm). Located directly in front of the outlet aperture 5 of the irradiation installation 1 is a radiation detector 7.

FIG. 2 illustrates the construction of a radiation monitor 8 which is connected to the radiation detector 7, by means of which there may be switched off a radiation dose which is to be applied upon the attainment of a preset reference value. The radiation monitor 8 contains a dose rate frequency converter 9 which is connected to the radiation detector 7, for example, a "Teledyne Philbrick" voltage-to-frequency converter 4701, whose output is connected to an impulse counter 10, for example, a "Motorola" BCD rate multiplier MC 14 527. Connected to the impulse counter is a presettable digital-comparator 11, for example, a "Motorola" 4-bit magnitude comparator MC 14 585. By means of this digital comparator, the automatic switch-off device 12 for the radiation installation which is connected to the output thereof, may be controlled as soon as the impulse counter 10 has reached the reference value which has been preset at the digital comparator 11.

For effecting drift correction there is now connected to the output of the dosage output-frequency converter 9 a second impulse counter 13, for example, a "Motorola" BCD rate multiplier MC 14 527, whose outputs are connected with a digital analog converter 14, for example, a "Hybrid Systems Corp." 8-bit, economy D/A Converter DAC 371. The output of this digital-analog-converter 14 is, in turn, reconveyed through a polarity inverter 15, for example, the bi-polar output range of the D/A Converter DAC 371, to the input of th- dose rate frequency converter 9. Hereby, an AND-gate 16, 17 is connected ahead of respectively each of the inputs of the two impulse counters 10, 13. Connected to the input of the second impulse counter 13, across an OR-gate 18, is a monostable flip-flop 19, for example, an "RCA" Cos/Mos low-power monostable/astable multivibrator CD 4047. The outputs 20, 21 thereof are connected to the second inputs of the two AND-gates 16, 17. The output 21 of the monostable flip-flop 19 which carries a signal in the stable position of the flip-flop, namely is connected to the second input of the AND-gate 16 which is connected ahead of the first impulse counter 10. The output 20 of the monostable flip-flop 19 which is inverse thereto is connected to the second input of the AND-gate 17 located ahead of the second input of the second impulse counter 13. Finally, the input of the dose rate frequency converter 9 is further connected to a potentiometer 22 through which the signal level may be imparted a potential voltage for avoiding the zero through-passage during the drift compensation.

Upon the actuation of the irradiation installation 1, an impulse (a so-called reset impulse) is conducted to the second input of the OR-gate 18, which tips the monostable flip-flop out of its stable condition and thereby closes the AND-gate 16 which is connected ahead of the first impulse counter 10, and releases the AND-gate 17 which is connected ahead of the impulse counter 13 and the monostable flip-flop 19. Through this reset-impulse, in a manner not described herein, also all count stages are moved back to zero through a corresponding input. Notwithstanding the actuation of the irradiation installation, the radiation remains switched off due to the missing signal at the output 21 of the monostable flip-flop 19. Thereby, the incoming signals, which can only be caused by drift, are transmitted only to the input of the monostable flip-flop 19 and of the second impulse counter 13 and are there counted. The output of this impulse counter controls the digital analog converter 14. The output signal of the latter is proportional to the count condition of the second impulse counter 13. The signal has its polarity reversed in the polarity inverter 15 and thereby lies at the input of the dose rate frequency converter 9 with an opposite sign. As long as impulses are still received at the input of the second impulse counter 13, these impulses are summed up and increase the voltage which is present at the output of the digital analog converter 14. This occurs for so long until this voltage, or respectively the voltage inverse thereto, has reached a value which compensates the drift of the components contained in this control circuit. As soon as no impulses any longer appear at the input of the second impulse counter 13 and the monostable flip-flop 19, the latter attains its stable condition at its own delay. It thereby blocks the AND-gate 17 ahead of the input of the second impulse counter 13 and opens the AND-gate 16 at the input of the first impulse counter 10.

Concurrently the radiation is released by means of the signal which is present at the output 21 of the monostable flip-flop 19. The impulses which are now received from the radiation detector 7 are transmitted across the drift-compensated components of the radiation monitor 8 to the first impulse counter 10, are there counted, and are employed through intermediary of the digital comparator 11 for the switching off of the irradiation or exposure installation upon attainment of the preset dosage reference value.

In the exemplary embodiment an AND-gate 16 is located ahead of the input of the first counter 10, which is controlled by the monostable flip-flop 19 so as to block this impulse counter 10 during the drift compensation. It is also possible to omit the AND-gate 16 and, in lieu thereof, to reset the first impulse counter 10 to "zero" after the effectuated drift compensation through the corresponding output signal of the monostable flip-flop 19 after effectuated drift compensation.

While there has been shown what is considered to be the preferred embodiment of the invention, it will be obvious that modifications may be made which come within the scope of the disclosure of the specification.

What is claimed is:

1. In a radiation monitor for an irradiation installation for the presetting of a radiation dosage which is to be applied and the limiting thereof to a preset reference value, including a radiation detector exposed to the radiation of said irradiation installation; a dose rate frequency converter connected to said radiation detector; a first impulse counter connected to an output of said dose rate frequency converter; a presettable digital comparator connected to the output of said first impulse counter; and automatic switch-off means for said installation controllable by said digital comparator responsive to reaching of said preset reference value, the improvement comprising: a second impulse counter having a digital analog converter connected to the output thereof for the drift correction of the electronic components of said installation and being connected to the output of said dose rate frequency converter; and a polarity inverter connected to the output of said digital analog converter, said digital analog converter output being connected across said polarity inverter to the input of said dose rate frequency converter.

2. A radiation monitor as claimed in claim 1, comprising an AND-gate connected to the input of each of said two impulse counters; an OR-gate connected to the input of said second impulse counter; and a monostable flip-flop connected in parallel with the input of said impulse counter across said OR-gate, the AND-gate connected the second input of said first impulse counter being connected to an output of said monostable flip-flop supporting a signal in the stable condition thereof, and the AND-gate connected to the second input of said second impulse counter being connected to the therewith inverted output of said monostable flip-flop.

3. A radiation monitor as claimed in claim 1, comprising a potential voltage being applied to the input of said dose rate frequency converter for effecting a zero-point suppression.

* * * * *